United States Patent [19]

Rodolfo

[11] Patent Number: 4,544,550

[45] Date of Patent: Oct. 1, 1985

[54] METHOD FOR THE TREATMENT OF DIABETES

[76] Inventor: Almanzor Y. Rodolfo, 806-F Paz Building Taft Ave., Manila, Philippines

[21] Appl. No.: 432,867

[22] Filed: Oct. 5, 1982

[51] Int. Cl.[4] .................... A61K 33/00; A61K 33/34; A61K 33/32; A61K 33/26
[52] U.S. Cl. .................................. 424/127; 424/140; 424/144; 424/147; 514/53; 514/866
[58] Field of Search ............... 424/127, 140, 144, 147, 424/180

[56] References Cited

PUBLICATIONS

Merck 9th ed., 1976, Chlorophyll.

*Primary Examiner*—Jerome D. Goldberg
*Assistant Examiner*—John W. Rollins, Jr.
*Attorney, Agent, or Firm*—Keil & Weinkauf

[57] ABSTRACT

A method for the treatment of diabetes is disclosed wherein the blood sugar of a patient in need of such treatment is lowered or reduced when an effective amount of an energizer composition containing basic food molecules and substances such as animal and plant proteins, carbohydrates, minerals, vitamins and thyroglobulin, is administered to the patient.

3 Claims, No Drawings

METHOD FOR THE TREATMENT OF DIABETES

This invention relates in general to the treatment of diabetes. More particularly, it relates to the method of lowering or reducing the blood sugar in the treatment of diabetes by administering an effective amount of an energizer composition comprising basic food molecules and substances such as animal and plant proteins, carbohydrates, minerals, vitamins and thyroglobulin.

BACKGROUND OF THE INVENTION

The energizer composition used in the present invention was discussed in my earlier Philippine Patent No. UM-4596 entitled "DIETARY SUPPLEMENT, TONIC AND ENERGIZER COMPOSITION". The composition was formulated to supply the body cells with food molecules, augment the electron transport system and to extract the free energy from the food molecules for endergonic cellular process.

All diseases result from or is a consequence of cell injury or cell necrosis. The present energizer composition contains a group of substances that increase the free energy content of injured cells. Free energy is the form of energy used by the cell for all its endergonic processes. Thermodynamics is a science that deals with energy flow. Therefore, the appropriate term to describe the management and treatment of the disease with this energizer composition is Thermodynamic Therapy. Energy generation and energy utilization occur in our cells. The currency of energy in our cells is Adenosinetriphosphate (ATP). The generation of energy occurs in the mitochondria, the power plant, the battery and transformer and respiratory center of the cell. This generated energy is what makes the cell perform its designed function.

The generation of ATP is made possible through oxidative phosphorylation within the cell mitochondria. The coupling of cellular respiration and the formation of high energy phosphate bonds is oxidative phosphorylation. The bulk of ATP formed is in the mitochondria and is generated through the citric acid cycle or krebs Cycle. The cycle is described as follows:

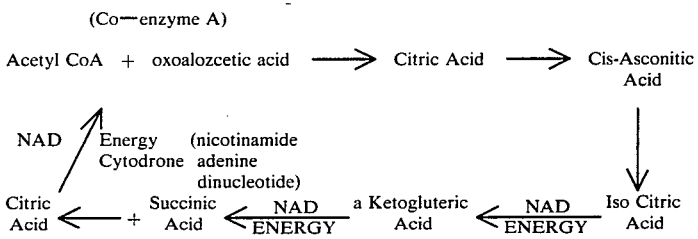

The final tetravalent reduction of molecular oxygen occurs along the electron transport chain located at the inner membrane of the mitochondria. The electron transport chain is described as follows:

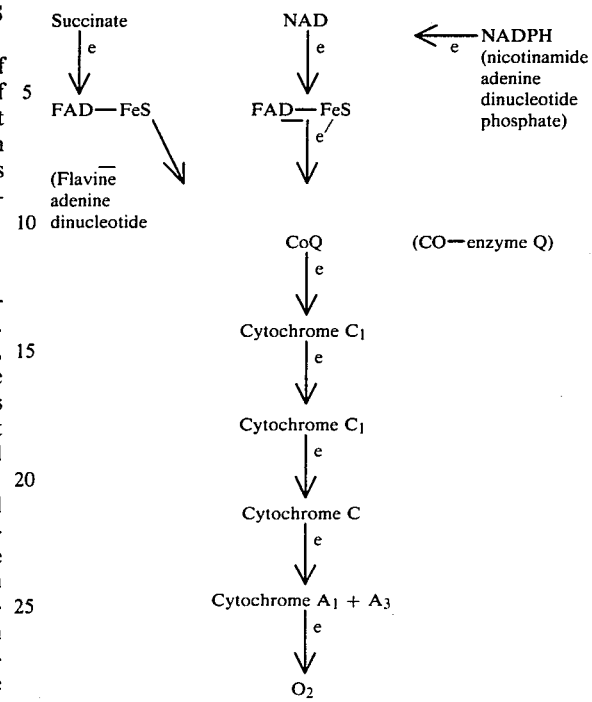

All these fundamental biochemical reactions occur in the mitochondria of cells. In the generation of ATP, the following basic factors must be present: (1) Molecular oxygen (2) efficient and adequate electron transport system (3) Integrity and efficiency of cellular mitochondria and (4) Adequate substrate (glucose) level.

The small amounts of vitamins, specially Vit. C, Pantoghenic Acid, Riboflavin, Vit. K, Iron and Manganese augments and makes efficient the electron transport system. Very small amounts of thyrogolbulin stimulates the mitochondria, and enough substrates (mono and disaccharides) tend to maximize the amount of free energy in the cells.

These are the energizing component of the product.

The fundamental basis of thermodyamic therapy with this energizer composition is the concept that the level of function and structural integrity of any cell is directly and proportionally dependent upon its free energy content. The mechanism of action of this energizer compound can be briefly stated as follows:

(1) It increases the peripheral molecular oxygen by its action on the red cells and form 2'5' diphosphoro glyceric acid which competes with oxygen in binding with hemoglobin and thereby increases the dissociation curve of oxyhemoglobin.

(2) It augments the electron transport system by supplying the major raw materials or substances for the synthesis of the enzyme of members of the electron transport system. (3) It stimulates the mitochondria, and (4) Indirectly it is a calcium complexing agent (calcium is a cellular respiratory inhibitor).

To test the validity of the concept of thermodynamic therapy with this energizer composition, the inventor has chosen for clinical research, those diseases and conditions whose current standard of management leave much to be desired, or those ridden with controversy or those which are empirical in nature. After several years of clinical trials, data and documents have been accumulated from excellent to good despite the severe constraints inherent in such a study.

During the clinical trials, it has been noted that a fair number of cases develop occasional episodes of hypoglycemia. The best corrective measure is to require cases under this therapy to take sugar can juice concentrate. Apparently, glucose utilization is maximized.

Several diseases have responded well to this energizer composition therapy but this invention will only be limited to the treatment of diabetes and the treatment for the other diseases will be presented at a later time as soon as concrete and convincing results have been established.

SUMMARY OF THE INVENTION

The object, therefore, of the present invention is to provide a method for lowering or reducing the blood sugar in the treatment of diabetes by using a medicinal preparation containing basic food molecules and substances such as animal and plant proteins, carbohydrates, minerals, vitamins and thyroglobulin.

Another object of this invention is to provide an energizer composition which can be not only used for the treatment of diabetes but also as dietary supplement, tonic and energizer, because of its nutritive value.

Other objects and advantageous features of this invention will become apparent from the reading of the description which will hereinafter be described in detail.

DESCRIPTION OF THE INVENTION

The present energizer composition is prepared from the following per capsule or tablet:

| Vitamin A | 85 i.u. |
| --- | --- |
| Vitamin D | 68 i.u. |
| Vitamin E | 1.7 i.u. |
| Vitamin C | 27.5 mg |
| Vitamin $B_1$ | 0.425 mg |
| Vitamin $B_2$ | 0.425 mg |
| Vitamin $B_6$ | 0.085 mg |
| Vitamin $B_{12}$ | 0.34 mg |
| Vitamin K | 1.66 mg to 8 mg |
| Niacinamide | 3.4 mg |

-continued

| Calcium Pantothenate | 0.85 mg |
| --- | --- |
| Iron | 1.5 mg |
| Calcium | 5.95 mg |
| Manganese | 0.17 mg |
| Potassium | 0.85 mg |
| Magnesium | 1.02 mg |
| Copper | 0.17 mg |
| Iodine | 0.0255 mg |
| Animal Protein | 83 mg to 95 mg |
| Plant Protein | 10 mg to 80 mg |
| Chlorophyllin | 1.5 mg |
| Thyroglobulin | 21.59 mg to 60 mg |
| Sugar | 114 mg |

The above components in their respective amounts are compounded and therafter encapsulating the same in a conventional encapsulating machine to produce the capsule product. The above composition can also be formulated in table form or other appropriate forms, but capsule is preferred.

The present composition is taken orally and the dosage is one to two capsules or tablets a day when used a a dietary supplement, tonic and energizer and one capsule or tablet two to three times a day when used for the treatment of diabetes.

Clinical tests were conducted on diabetic patients and the results are as follows:

| Patient | Age | Complaint | Treatment | Result |
| --- | --- | --- | --- | --- |
| 1 | 21 | 3 months pregnancy sugar 3+; diabetic, gastric pain, frequent urination | 1 cap. 2× a day for 15 days continue treatment monthly for examination | After 12 days sugar negative |
| 2 | 37 | 13 years diabetic, blood sugar - 380 | 1 cap. 3× a day for 2 months then 2 caps. a day for 6 months | Blood sugar went down to 110 2 months ago - still 110 6 months ago - normal diet |
| 3 | 63 | 25 years diabetic; blood sugar - 420 lowest is 210 | 1 cap. 3× a day; still 1 cap 3× a day | After 12 months, blood sugar went down to 130. |

It is to be understood that the above described method is but an illustrative applications of the principles of this invention and that numerous other modifications may be derived by those skilled in the art without departing from the spirit and scope of the appended claims.

Having thus described fully the scope covered by my invention, I now claim:

1. A method of reducing the blood sugar in the treatment of diabetes which comprises orally administering to a patient in need of such treatment an effective amount of a composition comprising the following ingredients in amounts proportional to the following amounts:

| Vitamin A | 85 i.u. |
| --- | --- |
| Vitamin D | 68 i.u. |
| Vitamin E | 1.7 i.u. |
| Vitamin C | 27.5 mg |
| Vitamin $B_1$ | 0.425 mg |
| Vitamin $B_2$ | 0.425 mg |
| Vitamin $B_6$ | 0.085 mg |
| Vitamin $B_{12}$ | 0.34 mg |
| Vitamin K | 1.66 mg to 8 mg |
| Niacinamide | 3.4 mg |
| Calcium Pantothenate | 0.85 mg |
| Iron | 1.5 mg |
| Calcium | 5.95 mg |
| Manganese | 0.17 mg |
| Potassium | 0.85 mg |
| Magnesium | 1.02 mg |

| -continued | |
|---|---|
| Copper | 0.17 mg |
| Iodine | 0.0255 mg |
| Animal Protein | 83 mg to 95 mg |
| Plant Protein | 10 mg to 80 mg |
| Chlorophyllin | 1.5 mg |
| Thyroglobulin | 21.59 mg to 60 mg |

| -continued | |
|---|---|
| Sugar | 114 mg |

2. The method of claim 1, wherein the composition comprises dosage units in tablet or capsule form comprising the ingredients in the specified amounts.

3. The method of claim 1, wherein the oral administration of an effective amount comprises orally administering a single dosage unit two to three times daily.

* * * * *